(12) United States Patent
Faarup

(10) Patent No.: US 6,653,492 B2
(45) Date of Patent: Nov. 25, 2003

(54) PREPARATION OF BILE ACIDS

(75) Inventor: Peter Faarup, Værløse (DK)

(73) Assignee: Novo Nordick A/S, Bagsvaerd (DK)

( * ) Notice: Subject to any disclaimer, the term of this patent is extended or adjusted under 35 U.S.C. 154(b) by 0 days.

(21) Appl. No.: 10/141,469

(22) Filed: May 1, 2002

(65) Prior Publication Data

US 2002/0183531 A1 Dec. 5, 2002

Related U.S. Application Data

(60) Provisional application No. 60/297,388, filed on Jun. 11, 2001.

(30) Foreign Application Priority Data

May 2, 2001 (DK) ........................................ 2001 00688

(51) Int. Cl.⁷ .................................................. C07J 9/00
(52) U.S. Cl. ...................................................... 552/552
(58) Field of Search ......................................... 552/552

(56) References Cited

U.S. PATENT DOCUMENTS 2,471,697 A * 5/1949 Minlon .................... 260/397.1

FOREIGN PATENT DOCUMENTS

| GB | 1527 605 | 10/1978 |
|---|---|---|
| WO | WO 95/07931 | 3/1995 |
| WO | WO 98/08871 | 3/1998 |

OTHER PUBLICATIONS

Martindale, The Extra Pharmacopoeia, CAS Apr. 25, 1981; 11006–55–6; pp. 1341–1342, 1993.
Campbell et al., J Am Chem Soc. vol. 79, pp. 1127–1129 (1957).
Bergman et al., Steroids, vol. 27, No. 3, pp. 431–437 (Mar. 1976).
Fieser et al., Steroids, p. 346 (1967).
JP 53108961 (WPI) Abstract, 1978.

* cited by examiner

Primary Examiner—Barbara P. Badio
(74) Attorney, Agent, or Firm—Reza Green, Esq.; Richard W. Boak, Esq.; Marc A. Began, Esq.

(57) ABSTRACT

Certain bile acids find use in the pharmaceutical industry. In view of the wide distribution of serious diseases such as HIV, AIDS and Bovine Spongiform Encephalopathy (BSE) it is desirable to avoid—as far as practicable—to have any components of animal origin in medicaments in order to eliminate any danger of infection. The present invention relates to a method of providing bile acids from non-animal starting materials.

11 Claims, No Drawings

PREPARATION OF BILE ACIDS

CROSS-REFERENCE TO RELATED APPLICATIONS

This application claims the benefit under 35 U.S.C. 119 of Danish applications PA 2001 00688 filed May 2, 2001, and of U.S. application Ser. No. 60/297,388 filed Jun. 11, 2001, the contents of which are hereby fully incorporated by reference.

FIELD OF THE INVENTION

The present invention relates to a method of providing bile acids from non-animal starting materials.

BACKGROUND OF THE INVENTION

Bile acids occur in conjugation with glycine or taurine in bile of most vertebrates and some of them find use in medicine. Thus, some bile acids—due to their inherent pharmacological properties—are used as cholerectics (see, for example, James E F Reynolds (editor) Martindale The Extra Pharmacopoeia, 30$^{th}$ Edition, The Pharmaceutical Press, London (1993), page 1341). Due to their surface-active properties bile acid salts have been tested as absorption enhancers in pharmaceutical compositions (GB 1,527, 605, Takeda). Also, bile acids can be used to make derivatives of therapeutic peptides with the purpose of influencing the profile of action of the peptides (WO 95/07931; WO 98/08871, both Novo Nordisk).

Traditionally, bile acids have been obtained from animal sources. However, the wide distribution of serious diseases such as HIV, AIDS and Bovine Spongiform Encephalopathy (BSE) has caused a wide spread fear that material of animal origin may cause infection. Even though the fear may not be well founded in all cases it is desirable to avoid—as far as practicable—to have any components of animal origin in medicaments in order to eliminate any danger and fear of danger. Bile acids have quite complicated molecular structures and they cannot be synthesized at a commercially acceptable price from simple starting materials.

DEFINITIONS

The designation "optionally substituted derivatives" of lithocholic acid and the intermediates used for its preparation is used to designate closely related products and intermediates which differ from lithocholic acid or the intermediates leading to lithocholic acid by having one or two further hydroxy groups (deoxycholic acid, chenodeoxycholic acid, cholic acid).

DESCRIPTION OF THE INVENTION

Natural products having some structural resemblance to the bile acids are found in the vegetable world and they are available at a price that does not from the outset forbid their use as starting materials in a large-scale synthesis of bile acids.

Accordingly, the present invention provides a method of providing lithocholic acid of Formula (I)

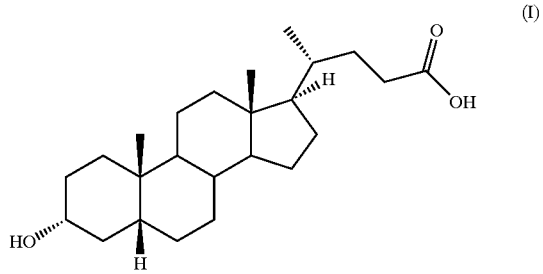

or an optionally substituted derivative thereof which comprises step a) catalytic hydrogenation of ethyl-3-oxo-4,22-choladienate (Formula (II)) or an optionally substituted derivative thereof

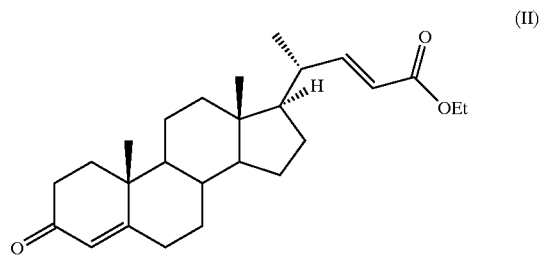

to give ethyl-3-oxocholanate (Formula (III)) or the corresponding substituted derivative thereof:

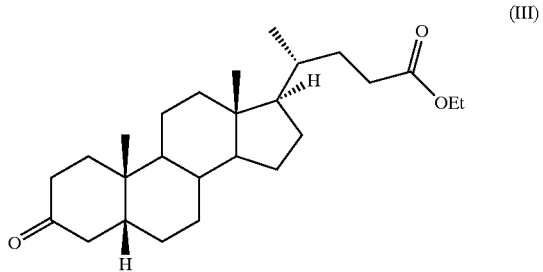

followed by:

step b) hydrolysis of the C-24 ester group of the intermediate of formula (III), obtained in step a), or the corresponding substituted derivative thereof, to give 3-oxocholanic acid (Formula (IV)) or the corresponding substituted derivative thereof,

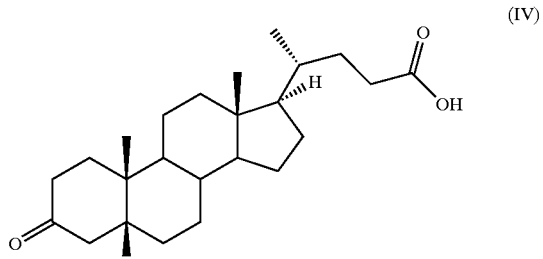

and reduction of the 3-keto group of this intermediate to give lithocholic acid (Formula (I)) or the corresponding substituted derivative thereof, or, as an alternative to step b):

step c) reduction of the 3-ketogroup of the intermediate (III), obtained in step a), or the corresponding substituted derivative thereof, to give the intermediate of formula (V):

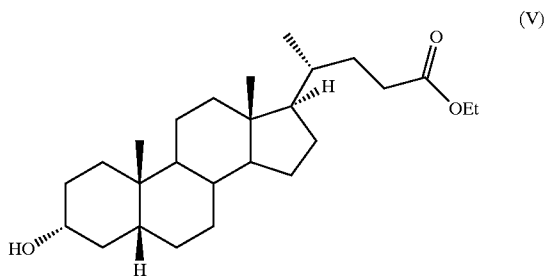

followed by hydrolysis of the C-24 ester group to give lithocholic acid (Formula (I)) or the corresponding substituted derivative thereof.

Stigmasterol is a sterol that can be isolated from soybeans. The above-mentioned starting material of formula (II) can be obtained from stigmasterol by oxidation and ozonolysis to 3-ketobisnor-4-cholenaldehyde as described by J A Campbell et al., J Am Chem Soc 79 (1957) 1127–1129, followed by reaction of the aldehyde with triethylphosphonoacetate as described by E D Bergmann et al., Steroids 27 (1976) 431–437.

The catalytic hydrogenation according to step a) above can be carried out in any suitable solvent conventionally used for catalytic hydrogenations e.g. alcohols and ethers. In one embodiment of the invention, the solvent used is 99% ethanol.

The catalyst used in step a) can be any catalyst that will provide specific reduction of the carbon—carbon double bonds in the 4-position and in the 22-position of the compound of formula (II) or a corresponding substituted derivative e.g. 5% palladium on carbon or 10% palladium on carbon. In one embodiment of the present invention the catalyst used for the reduction of the compound of formula (II) is 10% palladium on carbon.

The reduction described in step a) can be carried out in the presence of a base, such as an alkali metal hydroxide or an alkaline earth metal hydroxide or other metal hydroxide or such as an aliphatic amine, e.g. tert-butylamine. In a particular embodiment, the reduction is carried out in the presence of potassium hydroxide.

The reduction described in step a) can be carried out at various temperatures. In one embodiment of the present invention, the reduction is carried out at a temperature between 0° C. and 80° C. In a more specific embodiment the reduction is carried out at room temperature e.g. between 15° C. and 30° C.

The hydrogen pressure under which the reduction according to step a) is carried out can be selected within a wide range. Thus, in one embodiment, the pressure can be in the range from atmospheric pressure to 10 atmospheres. Other embodiments are at atmospheric pressure or in the range from atmospheric pressure to 2 atmospheres.

The hydrolysis of the ester group carried out according to step b) and step c) can be carried out under various conditions. Thus it can be carried out at room temperature in an alkaline mixture of water and a water miscible solvent e.g. an alcohol. When step b) is used, the base can conveniently be the base added before the catalytic hydrogenation was carried out. However, for the ester group hydrolysis a further amount of the same or another base can be added to the reaction mixture. When step c) is used, the reaction mixture in which the intermediate (V) is formed can be made strongly alkaline after dilution with water and hydrolysis of the ester group can be performed in this mixture. Alternatively, the intermediate (V) can be isolated and purified and subsequently the ester group can be hydrolysed e.g. using sodium hydroxide or potassium hydroxide in aqueous ethanol.

For the reduction of the 3-keto group in the intermediates of formula (III) and (IV) is used reducing agents that will provide a specific reduction of this group. Examples of such agents are lithium tri-tert-butoxyaluminiohydride, sodium borohydride and sodium borohydride combined with a modifying agent, e.g. cerium(III) chloride. The reductions are carried out starting at ice-bath temperature. Subsequently, the temperature is allowed to raise to room temperature. A convenient solvent when lithium tri-tert-butoxyaluminiohydride is used as the reducing agent is tetrahydrofuran. Other options are dioxane, ethylene glycol dimethyl ether and diethylene glycol dimethyl ether. A convenient solvent when sodium borohydride or sodium borohydride combined with a modifying agent is used as the reducing agent is methanol or ethanol optionally containing water.

EXAMPLES

Example 1

Preparation of lithocholic acid from stigmasterol

Stigmasterol obtained from soy beans is converted to 3-ketobisnor-4cholenaldehyde as described by J A Campbell et al., J Am Chem Soc 79 (1957) 1127–1129. The aldehyde is then reacted with triethylphosphonoacetate as described by E D Bergmann et al., Steroids 27 (1976) 431–437 to give ethyl 3-oxo-4,22-choladienate.

Preparation of 3-oxo-5β-cholan-24-oic acid:

Ethyl 3-oxo-4,22-choladienate (2.39 g) was dissolved in 99% ethanol (170 ml) containing 0.9 g of potassium hydroxide. 10% Palladium on carbon containing 50% $H_2O$ (0.16 g) was added and the mixture was hydrogenated at room temperature and 1 atmosphere for about 3 hours (280 ml hydrogen was consumed). The catalyst was removed by filtration and water (20 ml) was added. After stirring for 3 days, acetic acid was added to pH 4, the solution was concentrated under reduced pressure to about 10 ml, and 20 ml of water was added. After stirring, the mixture crystallised. Filtration and washing with water gave 2.1 g of the title compound. $^1$H-NMR (CDCl$_3$, 300 MHz), 0.67 (3H, s); 0.92 (3H, d); 1.00 (3H, s); 2.68 (1H, t).

Reduction of 3-oxo-5β-cholan-24-oic acid to lithocholic acid:

3-Oxo-5β-cholan-24-oic acid (3.0 g) was dissolved in dry tetrahydrofuran (40 ml), cooled on an ice-bath, and over 15 min. 17.5 ml of 1.1 M solution of Lithium tri-tert-butoxyaluminiohydride was added with stirring. Further 10 ml of tetrahydrofuran was added and stirring was continued for 15 min on an ice-bath and 1.5 hours at room temperature. After cooling the mixture on an ice-bath, the reaction was quenched by addition of 16 ml of water, followed by 20 ml of 6M HCl. The mixture was extracted with dichloromethane and the combined organic phases were washed with 1 M HCl and water and dried (Na$_2$SO$_4$). Removal of the solvent under reduced pressure gave 3.0 g of crude lithocholic acid. NMR analysis (CDCl$_3$, 300 MHz) of the product showed characteristic signal at 0.66 (3H,s); 0.93 (6H, s and d); 2.15–2.49 (2H, m); 3.63 (1H, m), in accordance with the $^1$H-NMR spectrum of reference lithocholic acid.

Example 2

Synthesis of $N^{\epsilon B29}$;ithocholoyl-γ-Glu des(B30) human insulin using N-lithocholoyl-Glu(OSu)-OH 1000 mg of des(B30) human insulin was dissolved in a mixture of 3.7 ml of water and 18.5 ml of N-methylpyrrolidone. The reaction vessel containing the solution was placed in a water bath equilibrated at 10° C. and the pH value of the solution was adjusted to 10.2 by addition of 4 M NaOH. 316 mg of N-lithocholoyl-Glu(OSu)-OH was dissolved in 2.6 ml of N-methylpyrrolidone at room temperature and 1 ml of triethanolamine was added. The dissolved reagent was then added to the insulin solution and allowed to react for 1 hour before the reaction was stopped by addition of 19 ml of 0.2 M ethanolamine adjusted to pH 9 by addition of 4 M HCl. The product was analysed by RP-HPLC against a standard of $N^{\epsilon B29}$lithocholoyi-γ-Glu des(B30) human insulin and the yield was 43%.

Example 3

Synthesis of $N^{\epsilon B29}$lithocholoyl-γ-Glu des(B30) human insulin using N-lithocholoyl-Glu(OSu)-O$^t$Bu.

3000 mg of des(B30) human insulin was dissolved in 150 ml of 50 mM boric acid in a reaction vessel, which was placed in a water bath equilibrated at 15° C. and the pH value of the solution was adjusted to 10.2 by addition of 4 M NaOH. 690 mg of N-lithocholoyl-Glu(OSu)-O$^t$Bu was dissolved in 150 ml acetonitrile heated to about 50° C. The dissolved reagent was then added to the insulin solution and allowed to react for 1 hour before the reaction was stopped by addition of 57 ml of 0.2 M ethanolamine adjusted to pH 9 by addition of 4 M HCl. Water was added to the reaction mixture to a final concentration of 20% v/v with respect to organic solvent and the pH value of the mixture was adjusted to 5.5 by addition of 4 M HCl. The reaction mixture was then left at 4° C. over night. The following day, the precipitated material was isolated by centrifugation and then freeze dried. The dried material was dissolved in 30 ml of trifluoroacetic acid in order to remove the O$^t$Bu protection group. The insulin material was then precipitated by addition of 10 volumes of acetone together with a few drops of concentrated HCl and subjected to purification. Yield: 1820 mg at a purity of 98.8%

Molecular mass, found by MS: 6193±6, theory: 6193

What is claimed is:

1. A method of producing lithocholic acid of formula (I)

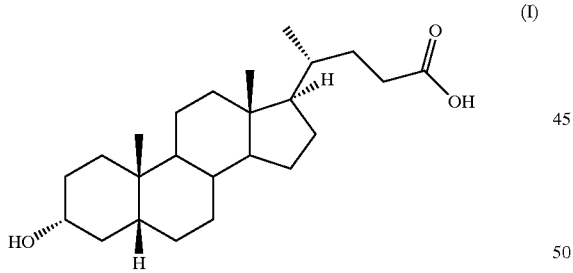

(I)

or an optionally substituted derivative thereof which comprises:

a) hydrogenating ethyl-3-oxo-4, 22-choladienate of Formula (II) or an optionally substituted derivative thereof in the presence of a catalyst

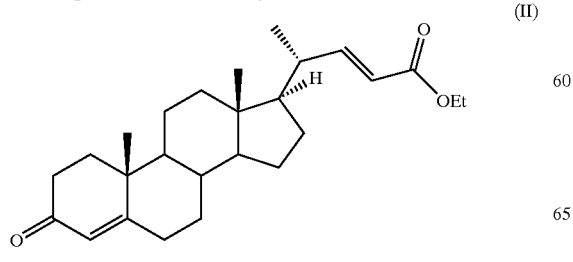

(II)

to give ethyl-3-oxocholanate of Formula (III) or the corresponding substituted derivative thereof:

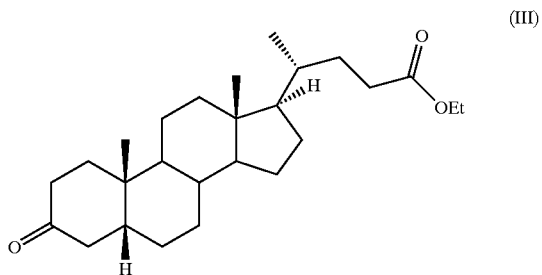

(III)

followed by:

b) hydrolyzing the C-24 ester group of the intermediate of formula (III) obtained in step a), or the corresponding substituted derivative thereof, to give 3-oxocholinic acid of Formula (IV) or the corresponding substituted derivative thereof,

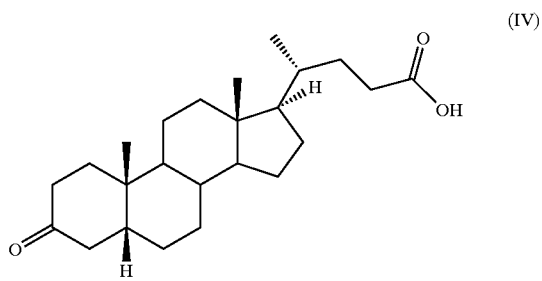

(IV)

and reduction of the 3-keto group of this intermediate to give lithocholic acid of Formula (I) or the corresponding substituted derivative thereof, or alternatively, c) reducing the 3-ketogroup of the intermediate (III), obtained in step a), or the corresponding substituted derivative thereof, to give the intermediate of formula (V):

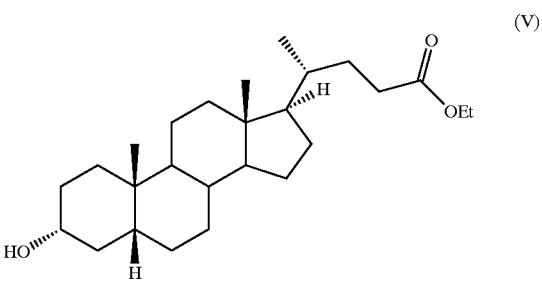

(V)

followed by hydrolysis of the C-24 ester group to give lithocholic acid of Formula (I) or the corresponding substituted derivative thereof.

2. The method of claim 1 wherein the hydrogenation in step a) is carried out under basic conditions.

3. The method of claim 2 wherein the hydrogenation is carried out in the presence of potassium hydroxide.

4. The method of claim 2 wherein the hydrogenation is carried out in the presence of an aliphatic amine.

5. The method of claim 1 wherein the hydrogenation in step a) is carried out at a temperature between 0° C. and 80°C.

6. The method of claim 1 wherein the hydrogenation in step a) is carried out under a hydrogen pressure of from 1 to 10 atmospheres.

7. The method of claim 1 wherein the catalyst is palladium on carbon.

8. The method of claim 1 wherein the hydrolysis in steps b) and c) is carried out in a mixture of water and a water-miscible, organic solvent containing potassium hydroxide or sodium hydroxide.

9. The method of claim 1 wherein the reducing agent used in steps b) and c) is selected from the group comprising lithium tri-tert-butoxyaluminiohydride, sodium borohydride and sodium borohydride in combination with a modifying agent.

10. The method of claim 9 wherein the modifying agent used in combination with sodium borohydride is cerium(III) chloride.

11. A method of producing lithocholic acid of formula (I)

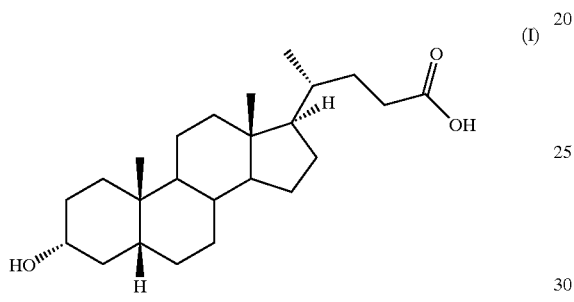

(I)

or a mono or di-hydroxy substituted derivative thereof which comprises:

a) hydrogenating ethyl-3-oxo-4, 22-choladienate of Formula (II) or a mono- or di-hydroxy substituted derivative thereof in the presence of a catalyst

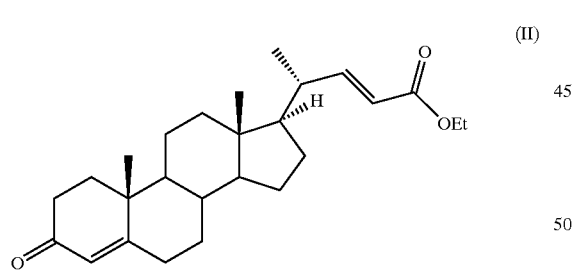

(II)

to give ethyl-3-oxocholanate of Formula (III) or the corresponding mono- or di-hydroxy substituted derivative thereof:

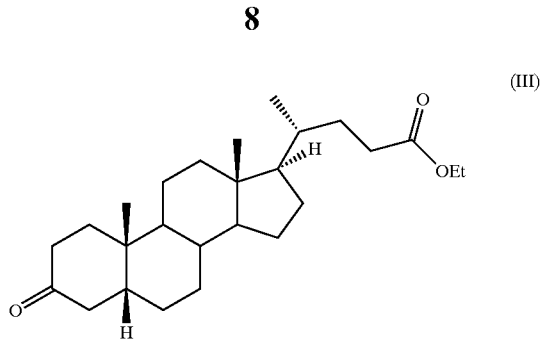

(III)

followed by:

b) hydrolyzing the C-24 ester group of the intermediate of Formula (III) obtained in step a), or the corresponding mono- or di-hydroxy substituted derivative thereof, to give 3-oxocholinic acid of Formula (IV) or the corresponding mono- or di-hydroxy substituted derivative thereof,

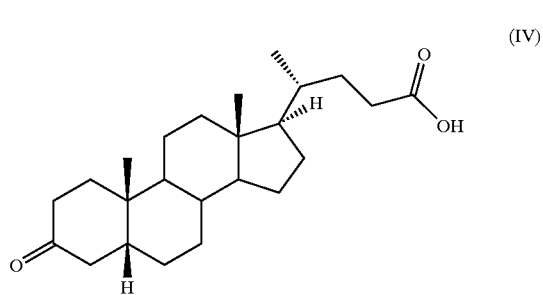

(IV)

and reduction of the 3-keto group of this intermediate to give lithocholic acid of Formula (I) or the corresponding substituted derivative thereof, or alternatively, c) reducing the 3-ketogroup of the intermediate (III), obtained in step a), or the corresponding mono- or di-hydroxy substituted derivative thereof, to give the intermediate of formula (V):

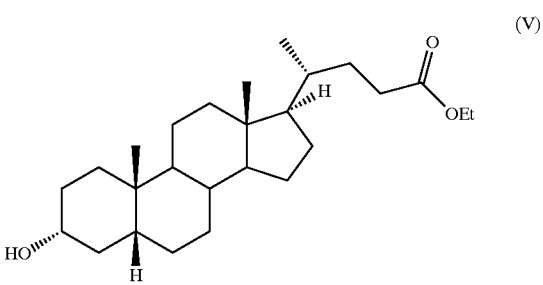

(V)

followed by hydrolysis of the C-24 ester group to give lithocholic acid of Formula (I) or the corresponding mono- or di-hydroxy substituted derivative thereof.

* * * * *